(12) United States Patent
Malhotra et al.

(10) Patent No.: US 10,709,715 B2
(45) Date of Patent: Jul. 14, 2020

(54) METHOD OF TREATING HYPERTENSION

(71) Applicant: Cipla Limited, Mumbai (IN)

(72) Inventors: Geena Malhotra, Mumbai (IN); Kalpana Joshi, Maharashtra (IN); Jeevan Ghosalkar, Maharashtra (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 16/207,597

(22) Filed: Dec. 3, 2018

(65) Prior Publication Data

US 2019/0167696 A1 Jun. 6, 2019

(30) Foreign Application Priority Data

Dec. 3, 2017 (IN) .............................. 201721043326

(51) Int. Cl.
| | | |
|---|---|---|
| *A61K 31/522* | (2006.01) | |
| *A61K 31/5575* | (2006.01) | |
| *A61K 31/5578* | (2006.01) | |
| *A61P 9/12* | (2006.01) | |
| *C07D 487/04* | (2006.01) | |
| *A61K 31/5585* | (2006.01) | |
| *A61K 31/513* | (2006.01) | |
| *A61K 9/00* | (2006.01) | |

(52) U.S. Cl.
CPC ........ *A61K 31/5585* (2013.01); *A61K 9/0053* (2013.01); *A61K 31/513* (2013.01); *A61K 31/522* (2013.01); *A61K 31/5575* (2013.01); *A61K 31/5578* (2013.01); *A61P 9/12* (2018.01); *C07D 487/04* (2013.01)

(58) Field of Classification Search
CPC ........................... C07D 487/04; A61K 31/522; A61K 31/5575; A61K 31/5578; A61P 9/12
USPC ........................................... 544/179; 514/183
See application file for complete search history.

(56) References Cited

U.S. PATENT DOCUMENTS

| | | | | | |
|---|---|---|---|---|---|
| 5,260,291 | A | * | 11/1993 | Lunt ..................... | A61K 31/52 514/183 |
| 7,579,336 | B2 | * | 8/2009 | Wang .................. | C07D 487/04 514/183 |

* cited by examiner

*Primary Examiner* — Venkataraman Balasubramanian
(74) *Attorney, Agent, or Firm* — Meunier Carlin & Curfman LLC

(57) ABSTRACT

Disclosed herein are methods of treating pulmonary hypertension, including pulmonary arterial hypertension, by administering to a patient in need thereof an effective amount of temozolomide, optionally in conjunction with one or more additional therapeutic agents. Compositions and kits including temozolomide for use in treating pulmonary hypertension, including pulmonary arterial hypertension, are also disclosed.

21 Claims, 5 Drawing Sheets

METHOD OF TREATING HYPERTENSION

CROSS-REFERENCE TO RELATED APPLICATION

This application claimed the benefit of Indian Application 201721043326, filed Dec. 3, 2017, the contents of which are hereby incorporated in its entirety.

FIELD OF THE INVENTION

The present invention relates to a method of treatment of pulmonary hypertension, including pulmonary arterial hypertension, by administering Temozolomide composition either alone or optionally in combination with one or more other agents. The present invention also pertains to compositions and kits useful for the treatment of pulmonary arterial hypertension in humans comprising Temozolomide or derivative thereof, alone or in combination with one or more drugs.

BACKGROUND

Pulmonary arterial hypertension (PAH), one of the five types of pulmonary hypertension (PH), is a life-threatening disease characterized by pulmonary vascular remodeling that leads to increased pulmonary vascular resistance and pulmonary arterial pressure, most often resulting in right-side heart failure. It is a progressive condition characterized by elevated pulmonary arterial pressures leading to right ventricular (RV) failure. It is defined at cardiac catheterization as a mean pulmonary artery pressure of 25 mm Hg or more. The most common symptom associated is breathlessness, with impaired exercise capacity as a hallmark of the disease.

Pulmonary hypertension can be classified as either primary or secondary. When the arterial hypertension is not accompanied, or caused by another underlying heart or lung disease or condition, it is called primary pulmonary arterial hypertension. When the arterial hypertension is triggered by another disease state, it is designated secondary arterial pulmonary hypertension. Exemplary conditions which can cause secondary pulmonary hypertension include congenital heart defects, ventricular or atrial septal defects/holes, which are in some cases called Eisenmenger complex, as well as valve conditions such as stenosis.

PAH is associated with significant morbidity and mortality. It is caused by complex pathways that culminate in structural and functional alterations of the pulmonary circulation and increases in pulmonary vascular resistance and pressure. Many mechanisms can lead to elevation of pulmonary pressures. In PAH, progressive narrowing of the pulmonary arterial bed results from an imbalance of vasoactive mediators, including prostacyclin, nitric oxide, and endothelin-1. This leads to an increased right ventricular afterload, right heart failure, and premature death. Diverse genetic, pathological, or environmental triggers stimulate PAH pathogenesis culminating in vasoconstriction, cell proliferation, vascular remodeling, and thrombosis. Current concepts suggest that PAH pathogenesis involves three primary processes: vasoconstriction, cellular proliferation/vascular remodeling, and thrombosis.

The molecular mechanism underlying PAH pathophysiology is not known yet, but it is believed that the endothelial dysfunction results in a decrease in the synthesis of endothelium-derived vasodilators such as nitric oxide and prostacyclin. Moreover, stimulation of the synthesis of vasoconstrictors such as thromboxane and vascular endothelial growth factor (VEGF) results in a severe vasoconstriction and smooth muscle and adventitial hypertrophy characteristic of patients with PAH.

Between 11% and 40% of patients with Idiopathic pulmonary arterial hypertension [IPAH] and 70% of patients with a family history of PAH carry a mutation in the gene encoding bone morphogenetic receptor-2 (BMPR2). However, penetrance is low, carriers have a 20% lifetime risk of developing pulmonary hypertension. Therefore, "multiple hits" are probably needed for the development of PAH. In pulmonary hypertension associated with left heart disease (PH-LHD), raised left atrial pressures result in secondary elevation of pulmonary pressure. In pulmonary hypertension owing to lung disease or hypoxia (PH-Lung), raised pulmonary arterial pressures result from mechanisms such as vascular destruction and hypoxic vasoconstriction. In chronic thromboembolic pulmonary hypertension [CTEPH], mechanical obstruction of the pulmonary vascular bed, is the primary process. Incidences are estimated to be 1-3.3 per million per year for IPAH and 1.75-3.7 per million per year for CTEPH; the prevalence of PAH is estimated at 15-52 per million. Pulmonary hypertension is more common in severe respiratory and cardiac disease, occurring in 18-50% of patients assessed for transplantation or lung volume reduction surgery, and in 7-83% of those with diastolic heart failure.

While there is currently no cure for PAH significant advances in the understanding of the pathophysiology of PAH have led to the development of several therapeutic targets. Besides conservative therapeutic strategies such as anticoagulation and diuretics, the current treatment paradigm for PAH targets the mediators of the three main biologic pathways that are critical for its pathogenesis and progression: (1) endothelin receptor antagonists inhibit the upregulated endothelin pathway by blocking the biologic activity of endothelin-1; (2) phosphodiesterase-5 inhibitors prevent breakdown and increase the endogenous availability of cyclic guanosine monophosphate, which signals the vasorelaxing effects of the down regulated mediator nitric oxide; and (3) prostacyclin derivatives provide an exogenous supply of the deficient mediator prostacyclin.

There are various drugs approved for the treatment of PAH: inotropic agents such as digoxin aids in the treatment by improving the heart's pumping ability. Nifedipine (Procardia) and Diltiazem (Cardizem) act as vasodilators and lowers pulmonary blood pressure and may improve the pumping ability of the right side of the heart Bosentan (Tracleer), ambrisentan (Letairis), macitentan (Opsumit), etc. are dual endothelin receptor antagonist that help to block the action of endothelin, a substance that causes narrowing of lung blood vessels. There are others which dilate the pulmonary arteries and prevent blood clot formation. Examples of such drugs are Epoprostenol (Veletri, Flolan), treprostinil sodium (Remodulin, Tyvaso), iloprost (Ventavis); PDE 5 inhibitors such as Sildenafil (Revatio), tadalafil (Adcirca), relax pulmonary smooth muscle cells, which leads to dilation of the pulmonary arteries.

Sildenafil is shown to be efficacious in therapy for humans with pulmonary arterial hypertension (Anna R Hemmes et al J. Expert Review of Cardiovascular Therapy, 4(3), 293-300, 2006)

U.S. Pat. No. 5,570,683 discloses method for treating or preventing reversible pulmonary vasoconstriction in a mammal such as PAH using combination of inhaled nitric oxide and therapeutically-effective amount of a phosphodiesterase inhibitor; wherein said phosphodiesterase inhibitor is administered before, during, or immediately after nitric oxide administration.

U.S. Pat. No. 7,893,050 discloses therapeutic combination, comprising an effective amount of fasudil and sildenafil, for treating pulmonary arterial hypertension.

European Patent No. EP 1097711B1 discloses use of Sildenafil in the manufacture of a medicament for treating or preventing pulmonary hypertension.

U.S. Pat. No. 8,324,247 discloses method for treating pulmonary arterial hypertension (PAH) by blocking both 5-HT2A and 5-HT2B receptors in a pulmonary artery such as N-Methyl-L-prolinol.

U.S. Pat. Nos. 9,474,752 and 8,377,933 discloses method for treating a pulmonary hypertension condition in a human patient, using combination of ambrisentan and agent selected from the group consisting of sildenafil, tadalafil and vardenafil.

Histamine stimulates only H1- and H2-receptors, since combined H1- and H2-receptor antagonism prevented almost all of the cardiovascular actions of histamine. (Tucker a. et al American J of Physiology, 229, 1008-1013, October 1975).

In addition to these established current therapeutic options, a large number of potential therapeutic targets are being investigated. These novel therapeutic targets include soluble guanylyl cyclase, phosphodiesterases, tetrahydrobiopterin, 5-hydroxytryptamine (serotonin) receptor 2B, vasoactive intestinal peptide, receptor tyrosine kinases, adrenomedullin, rho kinase, elastases, endogenous steroids, endothelial progenitor cells, immune cells, bone morphogenetic protein and its receptors, potassium channels, metabolic pathways, and nuclear factor of activated T cells.

Despite a certain success achieved in recent years, many patients with PAH are not adequately managed with existing therapies.

Thus, there is a need to provide a method of treating hypertension with the help of a drug which gives adequate therapeutic effect with minimal side effects and maximum therapeutic effect.

OBJECT OF THE INVENTION

It is an object of the invention to provide a novel therapeutic method for the treatment of pulmonary hypertension, including pulmonary arterial hypertension.

It is an object of the invention to provide novel compositions for the treatment of pulmonary hypertension, including pulmonary arterial hypertension.

It is an object of the invention to provide a novel therapeutic method for the treatment of pulmonary hypertension, including pulmonary arterial hypertension, using temozolomide.

It is an object of the invention to provide novel compositions for the treatment of pulmonary hypertension, including pulmonary arterial hypertension, comprising temozolomide.

SUMMARY

Disclosed herein are methods for treating pulmonary hypertension, for instance, pulmonary arterial hypertension, in patients in need thereof. In some instances, the methods include at least partial reduction of the symptoms associated with pulmonary hypertension, and in some instances, include completed elimination of the symptoms associated with pulmonary hypertension. The methods include the use of temozolomide or a derivative thereof for the treatment of pulmonary hypertension. Also, disclosed herein are compositions for the treatment of hypertension, wherein the compositions include Temozolomide or a derivative thereof.

The details of one or more embodiments are set forth in the descriptions below. Other features, objects, and advantages will be apparent from the description and from the claims.

DETAILED DESCRIPTION

Figure 1:
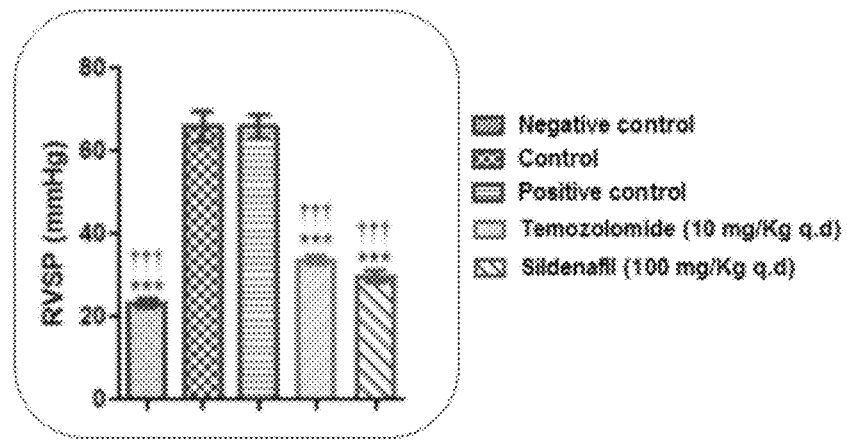
FIG. 1: Right Ventricular Systolic Pressure (RVSP) mmHg for Groups I, II, III, IV, V.
Figure 2:
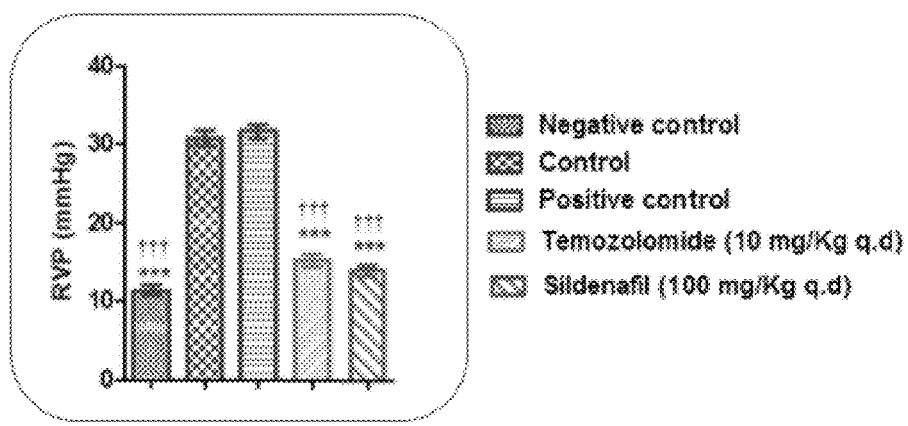
FIG. 2: Right Ventricular Pressure (RVP) mmHg for Groups I, II, III, IV, V.
Figure 3:
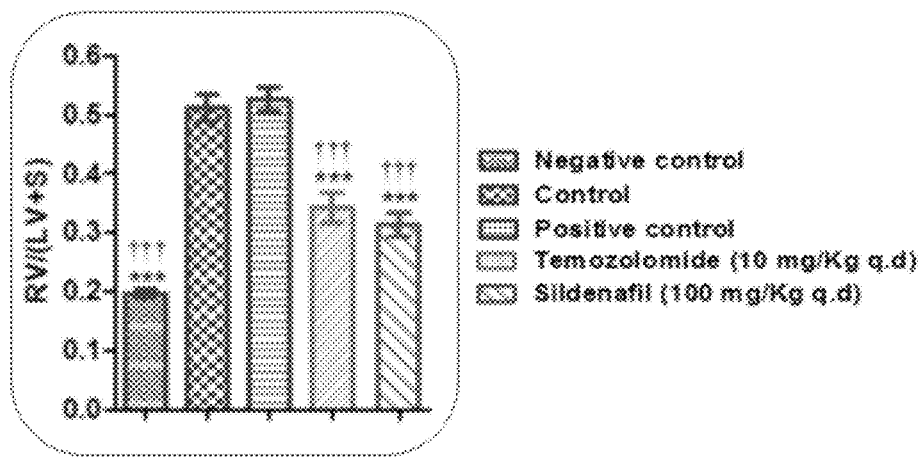
FIG. 3: Fulton index: Hypertrophy (RV/LV+S) for Groups I, II, III, IV, V.
Figure 4:
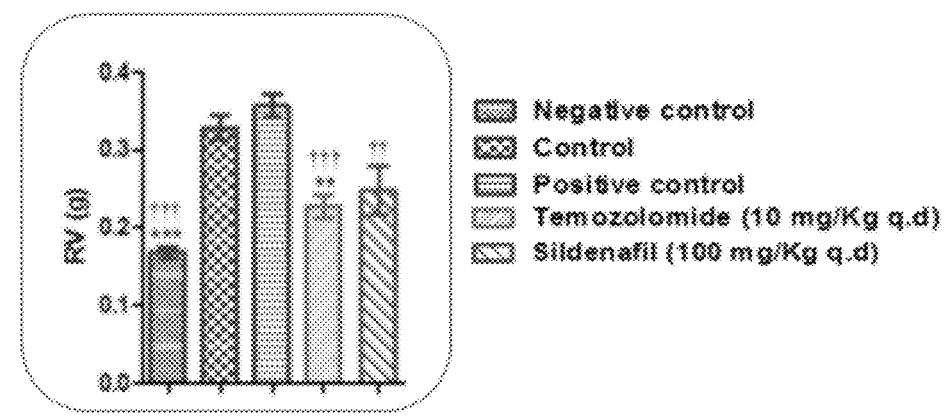
FIG. 4: Right Ventricle (RV) (g) for Groups I, II, III, IV, V.
Figure 5:
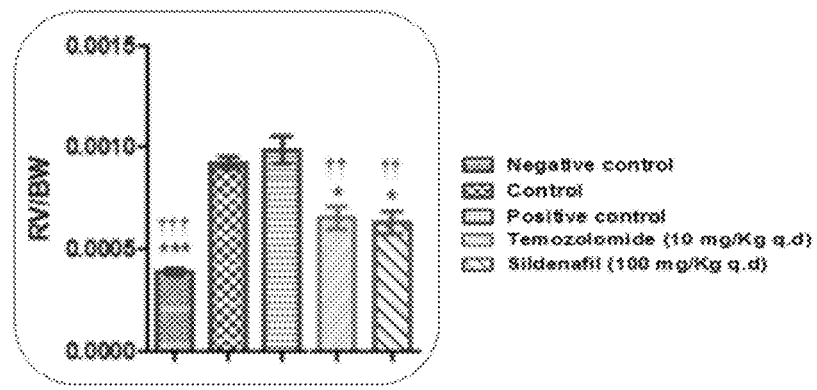
FIG. 5: Right Ventricle/body Weight (RV/BW) for Groups I, II, III, IV, V.
Figure 6:
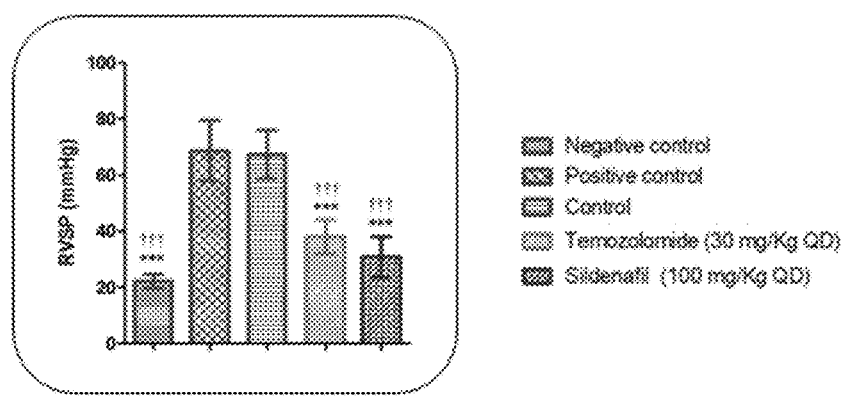
FIG. 6: Right Ventricular Systolic Pressure (RVSP) mmHg for Groups I, II, III, IV, V.
Figure 7:
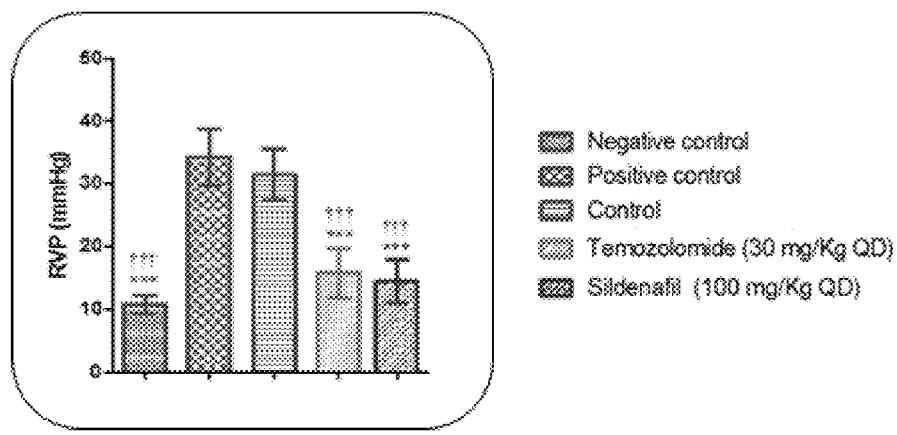
FIG. 7: Right Ventricular Pressure (RVP) mmHg for Groups I, II, III, IV, V.
Figure 8:
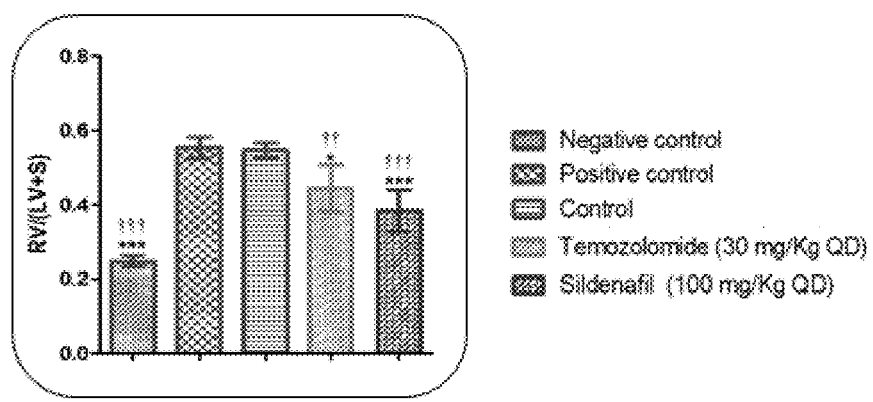
FIG. 8: Fulton index: Hypertrophy (RV/LV+S) for Groups I, II, III, IV, V.
Figure 9:
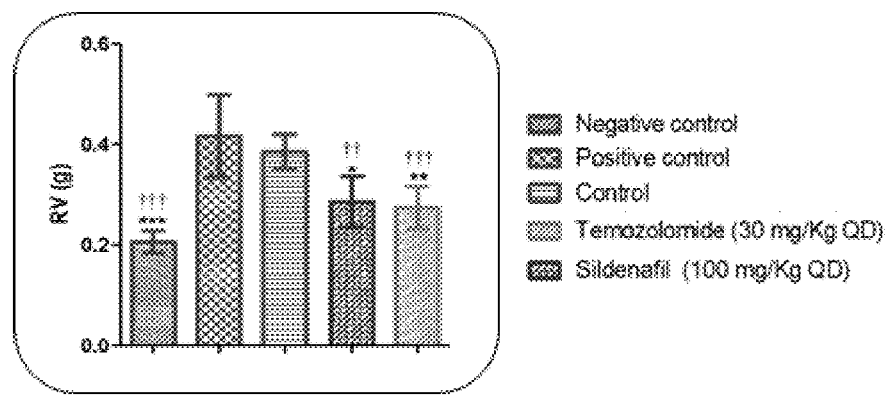
FIG. 9: Right Ventricle (RV) (g) for Groups I, II, III, IV, V.
Figure 10:
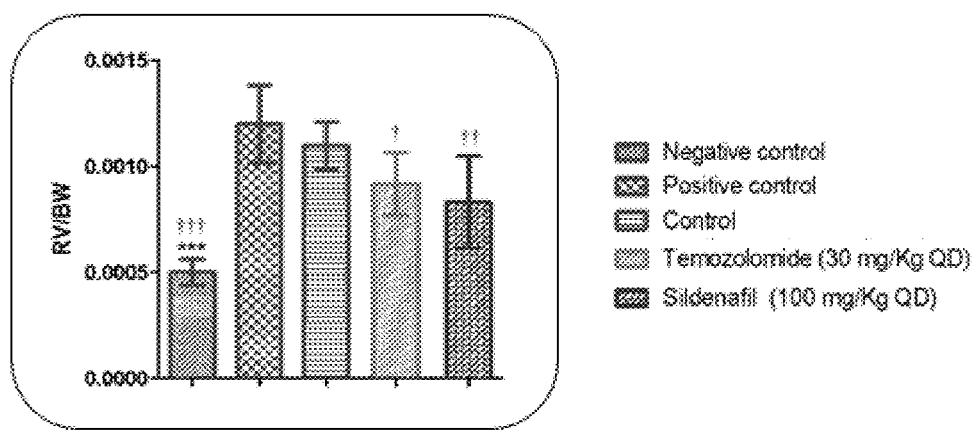
FIG. 10: Right Ventricle/body Weight (RV/BW) for Groups I, II, III, IV, V.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The inventors of the present invention while screening through several pharmacological agents surprisingly found through enormous experimentation and in vivo studies that temozolomide provides necessary control on pulmonary hypertension within the therapeutic range and thus can be used for treatment of pulmonary hypertension.

Pulmonary arterial hypertension (PAH) remains a mysterious killer that, like cancer, is characterized by tremendous complexity. PAH development occurs under sustained and persistent environmental stress, such as inflammation, shear stress, pseudo-hypoxia, and more. After inducing an initial death of the endothelial cells, these environmental stresses contribute with time to the development of hyper-proliferative and apoptotic resistant clone of cells including pulmonary artery smooth muscle cells, fibroblasts, and even pulmonary artery endothelial cells allowing vascular remodeling and PAH development. Molecularly, these cells exhibit many features common to cancer cells offering the opportunity to exploit therapeutic strategies used in cancer to treat PAH. Based on many points of overlap, among which deregulated cellular metabolism, sustained proliferation, and escape from apoptosis are the most predominant, PAH has emerged as a cancer-like disease.

Temozolomide is an alkylating drug indicated for the treatment of adult patients with:
1. Newly diagnosed glioblastoma multiforme (GBM) concomitantly with radiotherapy and then as maintenance treatment.
2. Refractory anaplastic astrocytoma patients who have experienced disease progression on a drug regimen containing nitrosourea and procarbazine.

Temozolomide is rapidly and completely absorbed after oral administration with a peak plasma concentration (Cmax) achieved in a median T max of 1 hour. Mean peak plasma concentration and AUC decreased by 32% and 9%, respectively, and median Tmax increased by 2-fold (from 1-2.25 hours) when temozolomide was administered after a modified high-fat breakfast. Temozolomide is chemically represented as—

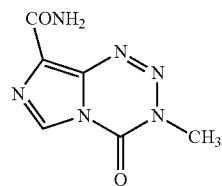

Temozolomide is not directly active but undergoes rapid nonenzymatic conversion at physiologic pH to the reactive compound 5-(3-methyltriazen-1-yl)-imidazole-4-carboxamide (MTIC). The cytotoxicity of MTIC is thought to be primarily due to alkylation of DNA. Alkylation (methylation) occurs mainly at the O6 and N7 positions of guanine.

Unless specified to the contrary, the term "temozolomide" embraces both the free base and pharmaceutically acceptable salts thereof.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, toluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made. Pharmaceutically acceptable cations include the cationic component of the acids listed above. Pharmaceutically acceptable anions include the anionic component of the bases listed above. In some preferred embodiments, Temozolomide (or a derivative thereof) is formulated as the salt.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of pulmonary arterial hypertension. Within the meaning of the present invention, the term "treat" also includes to arrest, delay the onset (i.e., the period prior to clinical manifestation of a disease) and/or reduce the risk of developing or worsening a disease. The term "combination" as used herein, defines either a fixed combination in one dosage unit form, a non-fixed combination or a kit containing individual parts for combined administration.

Pulmonary hypertension can be associated with left heart disease, or right heart disease. In some embodiments, temozolomide (or a derivative thereof) can be used to treat pulmonary hypertension associated with left heart disease, whereas in other embodiments, temozolomide (or a derivative thereof) can be used to treat pulmonary hypertension associated with right heart disease. In further embodiments, temozolomide (or a derivative thereof) can be used to treat pulmonary hypertension associated with both right and left heart disease. Temozolomide can be used to treat patients with sporadic idiopathic PAH, heritable PAH, as well as PAH due to disease of small pulmonary muscular arterioles.

Disclosed herein are methods for treating patients with pulmonary arterial hypertension. The hypertension may be mild (resting arterial pressure between 14-25 mm Hg) or complete (resting arterial pressure greater than 25 mm Hg). The patient to be treated may have a pulmonary arterial pressure greater than 14 mm Hg, greater than 16 mm Hg, greater than 18 mm Hg, greater than 20 mm Hg, greater than 22 mm Hg, greater than 24 mm Hg, greater than 26 mm Hg, greater than 28 mm Hg, greater than 30 mm Hg, greater than 32 mm Hg, greater than 34 mm Hg, greater than 36 mm Hg, greater than 38 mm Hg, or greater than 40 mm Hg.

In certain embodiments, temozolomide can be administered to patients with pulmonary arterial hypertension who are not also diagnosed with cancer, for instance brain cancer including glioblastoma or astrocytoma.

In some embodiments, temozolomide (or a derivative thereof) is administered to a patient (which may be a human or other mammal) in an amount sufficient to cause at least 5%, 10%, 15%, 20%, 25%, 30%, 35%, or 40% reduction in resting arterial pressure relative to the pulmonary arterial pressure prior to commencing treatment. In some instances, temozolomide (or a derivative thereof) is administered at a dose effective such that the patient's final resting arterial pressure is about 25 mm Hg, about 24 mm Hg, about 23 mm Hg, about 22 mm Hg, about 21 mm Hg, about 20 mm Hg, about 19 mm Hg, about 18 mm Hg, about 17 mm Hg, about 16 mm Hg, about 15 mm Hg, or about 14 mm Hg. In certain embodiments, Temozolomide (or a derivative thereof) is administered in combination with other agents, as described below, to achieve these therapeutic outcomes.

Pulmonary hypertension can be characterized by a pulmonary blood pressure greater than about 25 mm Hg at rest, and 30 mm Hg during exercise. Normal pulmonary arterial pressure is about 14 mm Hg at rest. In certain embodiments, temozolomide (or a derivative thereof) can be used to treat patients having a resting pulmonary arterial pressure of at least 20 mm Hg, at least 25 mm Hg, at least 30 mm Hg, at least 35 mm Hg, at least 40 mm Hg, at least 45 mm Hg, at least 50 mm Hg, at least 55 mm Hg, or at least 60 mm Hg.

In some instances, temozolomide may be administered to a patient a single time, while in other cases temozolomide can be administered using an intervallic dosing regimen. For instance, temozolomide may be administered once, twice, or three times a day for a period of at least 1 week, for example 2 weeks, 4 weeks, 6 weeks, 8 weeks, 10 weeks, 20 weeks, 40 weeks, or 52 weeks. In some instances, temozolomide administration can be suspended for some period of time (e.g., 1, 2, 3, 4, 6, 8, 10, 20, 40 or 52 weeks) followed by another period of administration.

In some instances, an initial dosage (higher dose, relative to maintenance dose) and maintenance doses (lower dose, relative to initial dose) may be specified. For instance, an initial dosage may be administered over the course of 1, 3, 5, 7, 10, 14, 21 or 28 days, followed by a maintenance dosage which is administered for the duration of the treatment. In some instances, the temozolomide can be administered to the patient using an interval greater than a day. For instance, the temozolomide can be administered once every other day, once every third day, once a week, once every two weeks, once every four weeks, once a month, once every other month, once every third month, once every six months, or once a year. In some instance, injectable formulations, such as depot formulations, are suitable for dosing regimens with extended periods in between administration, however, oral formulations can also be used in such systems.

The dosage and dosage regimen may be calculated per kg body weight. The dosage regimen may vary from a day to a month. Preferably, the composition as contemplated by the invention may be administered at least once, twice or thrice a day in the dosing range from 0.05 mg to about 30 mg per kg per day, 0.1 mg to about 10 mg per kg per day, 0.5 mg to about 10 mg per kg per day, 0.5 mg to about 5 mg per kg per day, 1 mg to about 5 mg per kg per day, or as per the requirement of the patient to be treated.

In some instances, the temozolomide (or a derivative thereof) may be administered to a patient a single time, while in other cases temozolomide (or a derivative thereof) can be administered using an intervallic dosing regimen. For instance, temozolomide (or a derivative thereof) may be administered once, twice, or three times a day for a period at least 1 week, for example 2 weeks, 4 weeks, 6 weeks, 8 weeks, 10 weeks, 20 weeks, 40 weeks, or 52 weeks. In some instances, temozolomide (or a derivative thereof) administration can be suspended for some period of time (e.g., 1, 2, 3, 4, 6, 8, 10, 20, 40 or 52 weeks) followed by another period of administration.

Preferably, temozolomide (or a derivative thereof) may be provided in the form of a pharmaceutical composition such as but not limited to, unit dosage forms including tablets, capsules (filled with powders, pellets, beads, mini-tablets, pills, micro-pellets, small tablet units, multiple unit pellet systems (MUPS), disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates), powders for reconstitution, transdermal patches and sprinkles, however, other dosage forms such as controlled release formulations, lyophilized formulations, modified release formulations, delayed release formulations, extended release formulations, pulsatile release formulations, dual release formulations and the like. Liquid or semisolid dosage form (liquids, suspensions, solutions, dispersions, ointments, creams, emulsions, microemulsions, sprays, patches, spot-on), injection preparations, parenteral, topical, inhalations, buccal, nasal etc. may also be envisaged under the ambit of the invention.

In some instances, temozolomide (or a derivative thereof) can be administered by inhalation, for instance as a powder or aerosolizable formulation.

The bioavailability of the drug in a composition, depends on various attributes of the drug as well as the other inactive ingredients in the formulation. The particle size of the drug is one of such attribute that may affect the bioavailability of the drug, when administered to a patient. The particle size may thus be adjusted as per the requirements of the invention.

The inventors of the present invention have also found that the solubility properties of temozolomide (or a derivative thereof) may be improved by nanosizing thus leading to better bioavailability and dose reduction of the drug.

In one embodiment, temozolomide (or a derivative thereof) may be present in the form of nanoparticles which have an average particle size of less than 2000 nm, less than 1500 nm, less than 1000 nm, less than 750 nm, or less than 500 nm.

Suitable excipients may be used for formulating the dosage forms according to the present invention such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, antimicrobial agents, antifoaming agents, emulsifiers, buffering agents, coloring agents, carriers, fillers, anti-adherents, solvents, taste-masking agents, preservatives, antioxidants, texture enhancers, channeling agents, coating agents or combinations thereof.

In some instances, the temozolomide (or a derivative thereof) can be administered to the patient using an interval greater than a day. For instance, Temozolomide (or a derivative thereof) can be administered once every other day, once every third day, once a week, once every two weeks, once every four weeks, once a month, once every other month, once every third month, once every six months, or once a year. In some instance, injectable formulations, such as depot formulations, are suitable for dosing regimens with extended periods in between administration, however, oral formulations can also be used in such systems.

In some embodiments, pulmonary arterial hypertension can be alleviated or treated by administration of temozolomide (or a derivative thereof) in combination with one or more other drugs either simultaneously, sequentially, or separately.

Preferably, one or more standard of care drugs that may be envisaged under the scope of the present invention may comprise from categories for the treatment of pulmonary hypertension such as, but not limited to phosphodiesterase inhibitors, endothelin receptor antagonist, Inotropic agents, and stimulators of soluble guanylate cyclase, such as riociguat.

Specifically, one or more standard of care drugs include but not limited to sildenafil, tadalafil, bosentan, ambrisentan, macitentan, nifedipine, diltiazem, digoxin. There are others which dilate the pulmonary arteries and prevent blood clot formation. Examples of such drugs are Epoprostenol (Veletri, Flolan), treprostinil sodium (Remodulin, Tyvaso), iloprost (Ventavis); PDE 5 inhibitors such as Sildenafil (Revatio), tadalafil (Adcirca), relaxes pulmonary smooth muscle cells, which leads to dilation of the pulmonary arteries.

The use of temozolomide may preferably be associated with one or more of the above referenced drugs as a combination therapy (either of the same functional class or other) depending on various factors like drug-drug compatibility, patient compliance and other such factors wherein the said combination therapy may be administered either simultaneously, sequentially, or separately for the treatment of PAH.

Temozolomide (or a derivative thereof) may be provided with one or more drugs in the form of a kit, wherein the kit includes temozolomide and at least one other drug, and instructions for their administration to a PAH patient.

In certain embodiments, the administration of temozolomide (or a derivative thereof), either alone or in combination with one or more drugs selected from but not limited to phosphodiesterase inhibitors such as sildenafil, tadalafil etc., endothelin receptor antagonist such as bosentan, macitentan etc. and stimulators of soluble guanylate cyclase such as riociguat. In certain embodiments, temozolomide (or a derivative thereof) can be co-administered with one or more additional agents effective to lower pulmonary hypertension. In some embodiments the co-administration includes a unitary dosage form containing temozolomide (or a derivative thereof) and at least one more agent. In other embodiments, temozolomide (or a derivative thereof) is administered separately from the other agent(s). The additional agent can be a PDE-5 inhibitor, for example, avanafil, lodenafil, mirodenafil, sildenafil, tadalafil, vardenafil, udenafil, zaprinast, or icariin. Other agents include calcium channel blockers like dihydropyridines (e.g., amlodipine, nifefipine) and diltiazem; prostacyclin pathway agonists such as epoprostenol, treprostinil, iloprost, and selexipag; endothelin receptor antagonists such as bosentan, macitentan, ambrisentan, and sitaxsentan; guanylate cyclase stimulators such as riociguat; diuretics; toprimate; fusadil; or anti-coagulants like warfarin.

It may be well appreciated by a person skilled in the art that the pharmaceutical composition comprising temozolomide in combination with one or more drugs may require specific dosage amounts and specific frequency of administrations specifically considering their individual established doses, the dosing frequency, patient adherence and the regimen adopted. As described herein, considering that there are various parameters to govern the dosage and administration of the combination composition as per the present invention, it would be well acknowledged by a person skilled in the art to exercise caution with respect to the dosage, specifically, for special populations associated with other disorders.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1—Monocrotaline Rat Model for Pulmonary Arterial Hypertension

The studies were conducted for hemodynamic evaluation of temozolomide in anesthetized sprague dawley rats treated with monocrotaline ("MCT") to induce pulmonary arterial hypertension. Sildenafil was used as an internal control to compare the effects of temozolomide.

The effects of temozolomide were evaluated in rats with monocrotaline induced pulmonary arterial hypertension using sildenafil as standard care treatment. Male Sprague-Dawley rats were orally administered vehicle, temozolomide (10 mg/kg given once daily every day for 28 days starting on Day 1), or sildenafil (100 mg/kg, administered once daily every day for 28 days starting on Day 1) (n=12 in each group). Rats received a single injection of monocrotaline (50 mg/kg, s.c.) on Study Day 1. On the twenty-eighth day following monocrotaline dosing, the rats were anesthetized with ketamine/xylazine for terminal monitoring of pulmonary and systemic arterial pressures along with heart rate.

Test Item: Vehicle (0.5% Methylcellulose+0.2% Tween 80 in deionized water, Temozolomide (10 mg/kg given once daily for 28 days; Sildenafil (100 mg/kg administered once daily)

Route of Administration: Oral

* is 0.5% methyl cellulose+0.2% Tween 80 in deionized water

Study Design: The study was planned and conducted according to design depicted below in Table 1

TABLE 1

Study Design

| Group number | Group name | n | MCT (S.C) | Test Compound | Dose (P.O) | Dosing |
|---|---|---|---|---|---|---|
| Group I | Negative control | 12 | — | Vehicle | 1 mL/Kg | QD |
| Group II | Control | 12 | 50 mg/Kg | MCT | — | |
| Group III | Vehicle control | 12 | 50 mg/Kg | Vehicle | 1 mL/Kg | QD |
| Group IV | Test group | 12 | 50 mg/Kg | Temozolomide | 10 mg/Kg | QD |
| Group V | Standard | 12 | 50 mg/Kg | Sildenafil | 100 mg/Kg | QD |

Pulmonary arterial hypertension was induced by injecting monocrotaline (3 mL/Kg MCT in 50% DMSO in water) subcutaneously at a dose of 50 mg/kg of body weight to all the randomized Male Sprague-Dawley rats of Groups II, III, IV and V (except negative control group). Negative control group (Group I, DMSO group) received a single dose of 3 mL/kg 50% DMSO in water for injection subcutaneously. The positive control group (Group III) received 5 ml of vehicle every morning. The rats of temozolomide group (Group IV) were orally administered temozolomide (10 mg/kg given once daily for 28 days starting on Day 1) and rats of sildenafil group (Group V) were orally administered sildenafil (100 mg/kg given once daily for 28 days starting on Day 1) On the twenty-eighth day after monocrotaline dosing, the rats were anesthetized with ketamine/xylazine for terminal monitoring of pulmonary and systemic arterial pressures along with heart rate.

Observation: There were differences in systolic and mean pulmonary arterial pressures after 28 days in rats treated with temozolomide at 10 mg/kg/day given once daily as compared to the vehicle group.

Results: Body weights among the vehicle and treatment cohorts were not significantly different at Study Day 28. There were differences in systolic and mean pulmonary arterial pressures after 28 days in rats treated with 10 mg/kg/QD/day temozolomide compared to the vehicle group.

The results are depicted in Table 2 (Right Ventricular Systolic Pressure); Table 3 (Right Ventricular Pressure) and Table 4 (Fulton index: Hypertrophy (RV/LV+S)); Table 5 (Right Ventricle (RV)); Table 6 (Right Ventricle/Body Weight)

TABLE 2

Right Ventricular Systolic Pressure

| | | | Right Ventricular Systolic Pressure (RVSP) mmHg | |
|---|---|---|---|---|
| Negative control | Control | Positive control | Temozolomide (10 mg/Kg) | Sildenafil (100 mg/Kg) |
| 20.652 | 58.059 | 70.816 | 40.220 | 34.262 |
| 25.143 | 81.052 | 61.444 | 33.582 | 25.579 |
| 17.995 | 57.290 | 77.630 | 27.895 | 33.864 |
| 27.854 | 78.538 | 59.801 | 29.626 | 23.627 |
| 25.161 | 62.606 | 72.949 | 33.857 | 31.322 |
| 21.357 | 60.018 | 60.142 | 35.059 | 24.486 |
| 20.936 | 72.695 | 56.082 | 38.531 | 29.450 |
| 23.622 | 57.327 | 68.670 | 30.456 | 31.316 |
| 24.461 | | | 30.333 | 32.922 |
| 25.580 | | | 36.128 | |
| 26.098 | | | 35.368 | |
| 20.773 | | | | |

TABLE 2-continued

Right Ventricular Systolic Pressure

| | | | Right Ventricular Systolic Pressure (RVSP) mmHg | |
|---|---|---|---|---|
| | Negative control | Control | Positive control | Temozolomide (10 mg/Kg) | Sildenafil (100 mg/Kg) |
| Mean | 23.303 | 65.948 | 65.942 | 33.732 | 29.648 |
| SD | 2.907 | 9.928 | 7.613 | 3.854 | 4.106 |
| SE | 0.839 | 3.510 | 2.692 | 1.162 | 1.369 |

Values are expressed as mean ± SE and analysed by one way ANOVA followed by Tukey's multiple comparison post-test.
* $P < 0.05$,  $P < 0.01$, * $P < 0.001$ as compared to control, + $P < 0.05$, ++ $P < 0.01$, +++ $P < 0.001$ as compared to positive control

TABLE 3

Right Ventricular Pressure

| | | | Right Ventricular Pressure (RVP) (mmHg) | |
|---|---|---|---|---|
| Negative control | Control | Positive control | Temozolomide (10 mg/Kg) | Sildenafil (100 mg/Kg) |
| 9.656 | 30.124 | 32.476 | 16.896 | 12.947 |
| 12.987 | 36.451 | 30.376 | 16.462 | 12.352 |
| 9.102 | 27.676 | 37.232 | 11.679 | 16.804 |
| 16.666 | 33.807 | 31.187 | 11.178 | 11.481 |
| 12.701 | 29.169 | 30.585 | 15.927 | 15.226 |
| 9.210 | 30.734 | 31.389 | 16.493 | 11.673 |
| 8.251 | 29.384 | 28.909 | 19.994 | 14.427 |
| 11.448 | 28.386 | 31.214 | 15.532 | 14.139 |
| 12.402 | | | 12.593 | 16.310 |
| 12.866 | | | 16.840 | |
| 10.947 | | | 17.431 | |
| 9.645 | | | | |

| | Negative control | Control | Positive control | Temozolomide (10 mg/Kg) | Sildenafil (100 mg/Kg) |
|---|---|---|---|---|---|
| Mean | 11.323 | 30.716 | 31.671 | 15.548 | 13.929 |
| SD | 2.361 | 2.967 | 2.466 | 2.673 | 1.951 |
| SE | 0.682 | 1.049 | 0.872 | 0.806 | 0.650 |

Values are expressed as mean ± SE and analysed by one way ANOVA followed by Tukey's multiple comparison post-test.
* $P < 0.05$,  $P < 0.01$, * $P < 0.001$ as compared to control, + $P < 0.05$, ++ $P < 0.01$, +++ $P < 0.001$ as compared to positive control

TABLE 4

Fulton index: Hypertrophy (RV/LV + S)

| | | | Fulton index: Hypertrophy (RV/LV + S) | |
|---|---|---|---|---|
| Negative control | Control | Positive control | Temozolomide (10 mg/Kg) | Sildenafil (100 mg/Kg) |
| 0.181 | 0.619 | 0.604 | 0.519 | 0.330 |
| 0.179 | 0.482 | 0.499 | 0.345 | 0.167 |
| 0.166 | 0.493 | 0.518 | 0.273 | 0.354 |
| 0.180 | 0.471 | 0.534 | 0.325 | 0.367 |
| 0.206 | 0.588 | 0.614 | 0.333 | 0.297 |
| 0.200 | 0.426 | 0.508 | 0.450 | 0.323 |
| 0.202 | 0.513 | 0.483 | 0.294 | 0.312 |
| 0.211 | 0.494 | 0.446 | 0.406 | 0.352 |

TABLE 4-continued

Fulton index: Hypertrophy (RV/LV + S)

Fulton index: Hypertrophy (RV/LV + S)

| | Negative control | Control | Positive control | Temozolomide (10 mg/Kg) | Sildenafil (100 mg/Kg) |
|---|---|---|---|---|---|
| | 0.162 | | | 0.287 | 0.309 |
| | 0.228 | | | 0.277 | |
| | 0.213 | | | 0.255 | |
| | 0.231 | | | | |
| Mean | 0.197 | 0.511 | 0.526 | 0.342 | 0.312 |
| SD | 0.023 | 0.063 | 0.058 | 0.083 | 0.059 |
| SE | 0.007 | 0.022 | 0.020 | 0.025 | 0.020 |

Values are expressed as mean ± SE and analysed by one way ANOVA followed by Tukey's multiple comparison post-test.
* $P < 0.05$,  $P < 0.01$, * $P < 0.001$ as compared to control, + $P < 0.05$, ++ $P < 0.01$, +++ $P < 0.001$ as compared to positive control.

TABLE 5

Right Ventricle

Right ventricle (RV) (g)

| | Negative control | Control | Positive control | Temozolomide (10 mg/Kg) | Sildenafil (100 mg/Kg) |
|---|---|---|---|---|---|
| | 0.160 | 0.337 | 0.378 | 0.311 | 0.261 |
| | 0.178 | 0.336 | 0.320 | 0.220 | 0.083 |
| | 0.127 | 0.227 | 0.300 | 0.156 | 0.236 |
| | 0.140 | 0.327 | 0.390 | 0.244 | 0.440 |
| | 0.180 | 0.347 | 0.419 | 0.220 | 0.228 |
| | 0.180 | 0.349 | 0.322 | 0.298 | 0.207 |
| | 0.190 | 0.317 | 0.387 | 0.202 | 0.232 |
| | 0.177 | 0.386 | 0.333 | 0.268 | 0.308 |
| | 0.124 | | | 0.218 | 0.229 |
| | 0.185 | | | | 0.197 |
| | 0.170 | | | | 0.167 |
| | 0.205 | | | | |
| Mean | 0.168 | 0.328 | 0.356 | 0.227 | 0.247 |
| SD | 0.025 | 0.046 | 0.043 | 0.049 | 0.094 |
| SE | 0.007 | 0.016 | 0.015 | 0.015 | 0.031 |

Values are expressed as mean ± SE and analysed by one way ANOVA followed by Tukey's multiple comparison post-test.
* $P < 0.05$,  $P < 0.01$, * $P < 0.001$ as compared to control, + $P < 0.05$, ++ $P < 0.01$, +++ $P < 0.001$ as compared to positive control.

TABLE 6

Right Ventricle/Body Weight

RV/Body wt

| | Negative control | Control | Positive control | Temozolomide (10 mg/Kg) | Sildenafil (100 mg/Kg) |
|---|---|---|---|---|---|
| | 0.0004 | 0.0010 | 0.0012 | 0.0011 | 0.0007 |
| | 0.0004 | 0.0010 | 0.0009 | 0.0007 | 0.0003 |
| | 0.0003 | 0.0009 | 0.0009 | 0.0005 | 0.0007 |
| | 0.0004 | 0.0009 | 0.0012 | 0.0006 | 0.0009 |
| | 0.0004 | 0.0010 | 0.0012 | 0.0006 | 0.0006 |
| | 0.0004 | 0.0009 | 0.0008 | 0.0008 | 0.0006 |
| | 0.0004 | 0.0008 | 0.0009 | 0.0006 | 0.0006 |
| | 0.0005 | 0.0009 | 0.0008 | 0.0008 | 0.0007 |
| | 0.0003 | | | 0.0005 | 0.0006 |
| | 0.0004 | | | 0.0005 | |
| | 0.0004 | | | 0.0005 | |
| | 0.0004 | | | | |
| Mean | 0.0004 | 0.0009 | 0.0010 | 0.0007 | 0.0006 |
| SD | 0.0000 | 0.0001 | 0.0002 | 0.0002 | 0.0002 |
| SE | 0.0000 | 0.0000 | 0.0001 | 0.0001 | 0.0001 |

Values are expressed as mean ± SE and analysed by one way ANOVA followed by Tukey's multiple comparison post-test.
* $P < 0.05$,  $P < 0.01$, * $P < 0.001$ as compared to control, + $P < 0.05$, ++ $P < 0.01$, +++ $P < 0.001$ as compared to positive control The results suggest that Temozolomide activity in controlling or reducing PAH was found to be comparable among with Sildenafil activity.

Example 2: Monocrotaline Rat Model for Treatment of Pulmonary Arterial Hypertension The studies were conducted for hemodynamic evaluation of Temozolomide in anesthetized Sprague Dawley rats treated with monocrotaline ("MCT") to induce pulmonary arterial hypertension. Sildenafil was used as an internal control to compare the effects of temozolomide The effects of temozolomide were evaluated in rats with monocrotaline induced pulmonary arterial hypertension using sildenafil as standard care treatment. Male Sprague-Dawley rats were orally administered vehicle, temozolomide (30 mg/kg, given once daily every day starting on Day 14 till Day 28), or sildenafil (100 mg/kg, given once daily every day starting on Day 14 till Day 28) (n=12 in each group). Rats received a single injection of monocrotaline (50 mg/kg, s.c.) on Study Day 1. On the twenty-eighth day following monocrotaline dosing, the rats were anesthetized with ketamine/xylazine for terminal monitoring of pulmonary and systemic arterial pressures along with heart rate.

Test Item: Vehicle (0.5% Methylcellulose+0.2% Tween 80 in deionized water, temozolomide (30 mg/kg given once daily starting on Day 14 till Day 28; Sildenafil (100 mg/kg, administered once daily starting on Day 14 till Day 28)

Route of Administration: Oral

\* is 0.5% methyl cellulose+0.2% Tween 80 in deionized water

Study Design: The study was planned and conducted according to design depicted below in Table 7

TABLE 7

Study Design

| Group number | Group name | n | MCT (S.C) | Test Compound | Dose (P.O) | Dosing |
|---|---|---|---|---|---|---|
| Group VI | Negative control | 12 | — | Vehicle | 5 mL/Kg | QD |
| Group VII | Control | 12 | 50 mg/Kg | MCT | — | |
| Group VIII | Positive control | 12 | 50 mg/Kg | Vehicle | 5 mL/Kg | QD |
| Group IX | Test group | 12 | 50 mg/Kg | Temozolomide | 30 mg/Kg | QD |
| Group X | Standard | 12 | 50 mg/Kg | Sildenafil | 100 mg/Kg | QD |

Pulmonary arterial hypertension was induced by injecting 50 mg/kg dose of monocrotaline (3 mL/Kg MCT in 50% DMSO in water) subcutaneously to all the randomized Male Sprague-Dawley rats of Groups VII, VIII, IX, and X (except negative control group). Negative control group (Group VI, DMSO group) received a single dose of 3 mL/kg 50% DMSO in water for injection subcutaneously. Male Sprague-Dawley rats in groups VII, VIII, IX, and X were administered 50 mg/kg of body weight of monocrotaline in DMSO subcutaneously to induce PAH on day 1. The rats of vehicle positive control group (Group VIII) received 5 ml of vehicle every morning. The rats of the temozolomide group (Group IX) were orally administered Temozolomide (30 mg/kg given once daily starting on Day 14 till Day 28) and rats of sildenafil group (Group X) were orally administered sildenafil (100 mg/kg given once daily starting on Day 14 till Day 28). On the twenty-eighth day after monocrotaline dosing, the rats were anesthetized with ketamine/xylazine for terminal monitoring of pulmonary and systemic arterial pressures along with heart rate. It is understood that from day 1 till administration of test compounds i.e till day 14, rates of all groups were suffering from PAH due to administration of MCT. Thus the study was conducted to evaluate the efficacy of Temozolomide treatment for PAH. Sildenafil was used as an internal control to compare the effects of Temozolomide.

Observation: There were differences in systolic and mean pulmonary arterial pressures after 28 days in rats treated with temozolomide at 30 mg/kg/day given once daily as compared to the vehicle group.

Results: Body weights among the vehicle and treatment cohorts were not significantly different at Study Day 28. There were differences in systolic and mean pulmonary arterial pressures after 28 days in rats treated with 30 mg/kg/QD/day temozolomide compared to the vehicle group.

The results are depicted in Table 8 (Right Ventricular Systolic Pressure); Table 9 (Right Ventricular Pressure) and Table 10 (Fulton index: Hypertrophy (RV/LV+S)); Table 11 (Right Ventricle (RV)); Table 12 (Right Ventricle/Body Weight)

TABLE 8

Right Ventricular Systolic Pressure
Right Ventricular Systolic Pressure (RVSP) mmHg

| Animal no | Negative control | Positive control | Control | Temozolomide (30 mg/Kg) | Sildenafil (100 mg/Kg) |
|---|---|---|---|---|---|
| 1 | 20.794 | | | | |
| 2 | 24.496 | | | 29.989 | |
| 3 | 18.414 | 64.680 | | 33.218 | 36.579 |
| 4 | 22.133 | | | | |
| 5 | 22.287 | | 74.837 | 39.693 | |
| 6 | 26.614 | | 62.653 | 42.429 | 22.951 |
| 7 | 19.890 | 49.886 | | 31.561 | |
| 8 | 25.473 | 75.948 | 70.280 | 36.888 | 27.908 |
| 9 | 22.665 | 84.635 | | 37.763 | |
| 10 | 21.267 | 72.233 | 73.574 | 48.504 | 33.917 |
| 11 | 21.677 | 67.349 | 52.116 | 45.392 | 23.264 |
| 12 | 20.082 | 66.064 | 70.439 | 33.928 | 40.201 |
| Mean | 22.149 | 68.685 | 67.316 | 37.936 | 30.803 |
| SD | 2.392 | 10.784 | 8.568 | 6.090 | 7.187 |
| SE | 0.691 | 4.076 | 3.498 | 1.926 | 2.934 |
| % Inhibition | | 0.00 | 1.99 | 44.77 | 55.15 |

Values are expressed as mean ± SE and analysed by one way ANOVA followed by Tukey's multiple comparison post-test.
* $P < 0.05$,  $P < 0.01$, * $P < 0.001$ as compared to control, + $P < 0.05$, ++ $P < 0.01$, +++ $P < 0.001$ as compared to positive control

TABLE 9

Right Ventricular Pressure
Right Ventricular Pressure (RVP) mmHg

| Animal no | Negative control | Positive control | Control | Temozolomide (30 mg/Kg) | Sildenafil (100 mg/Kg) |
|---|---|---|---|---|---|
| 1 | 9.520 | | | | |
| 2 | 10.471 | | | 12.363 | |
| 3 | 8.625 | 36.264 | | 12.035 | 18.486 |
| 4 | 9.953 | | | | |
| 5 | 10.522 | | 33.768 | 15.151 | |
| 6 | 13.042 | | 25.741 | 19.476 | 10.916 |
| 7 | 9.513 | 25.929 | | 14.308 | |
| 8 | 13.434 | 34.125 | 36.147 | 12.295 | 11.268 |
| 9 | 11.614 | 38.020 | | 15.993 | |
| 10 | 12.064 | 37.707 | 33.058 | 21.577 | 17.424 |
| 11 | 10.989 | 30.733 | 26.937 | 22.479 | 11.506 |
| 12 | 9.767 | 37.265 | 32.993 | 12.349 | 16.211 |
| Mean | 10.793 | 34.292 | 31.441 | 15.802 | 14.302 |
| SD | 1.485 | 4.489 | 4.132 | 4.005 | 3.446 |
| SE | 0.429 | 1.697 | 1.687 | 1.267 | 1.407 |
| % Inhibition | | 0.00 | 8.31 | 53.92 | 58.29 |

Values are expressed as mean ± SE and analysed by one way ANOVA followed by Tukey's multiple comparison post-test.
* $P < 0.05$,  $P < 0.01$, * $P < 0.001$ as compared to control, + $P < 0.05$, ++ $P < 0.01$, +++ $P < 0.001$ as compared to positive control

TABLE 10

Fulton index
Fulton index : Hypertrophy (RV/LV + S)

| Animal no | Negative control | Positive control | Control | Temozolomide (30 mg/Kg) | Sildenafil (100 mg/Kg) |
|---|---|---|---|---|---|
| 1 | 0.254 | | | | |
| 2 | 0.232 | | | 0.481 | |
| 3 | 0.233 | 0.524 | | 0.502 | 0.464 |
| 4 | 0.242 | | | | |
| 5 | 0.264 | | 0.567 | 0.480 | |
| 6 | 0.236 | | 0.527 | 0.481 | 0.393 |
| 7 | 0.244 | 0.518 | | 0.382 | |
| 8 | 0.274 | 0.576 | 0.540 | 0.357 | 0.306 |
| 9 | 0.267 | 0.598 | | 0.485 | |
| 10 | 0.233 | 0.565 | 0.547 | 0.506 | 0.337 |
| 11 | 0.260 | 0.554 | 0.570 | 0.341 | 0.389 |
| 12 | 0.240 | 0.542 | 0.524 | 0.427 | 0.415 |
| Mean | 0.248 | 0.554 | 0.546 | 0.444 | 0.384 |
| SD | 0.015 | 0.029 | 0.019 | 0.063 | 0.056 |
| SE | 0.004 | 0.011 | 0.008 | 0.020 | 0.023 |
| % Inhibition | | 0.00 | 1.47 | 19.83 | 30.70 |

Values are expressed as mean ± SE and analysed by one way ANOVA followed by Tukey's multiple comparison post-test.
* $P < 0.05$,  $P < 0.01$, * $P < 0.001$ as compared to control, + $P < 0.05$, ++ $P < 0.01$, +++ $P < 0.001$ as compared to positive control

TABLE 11

Right Ventricle weight
Right Ventricle weight (gms)

| Animal no | Negative control | Positive control | Control | Temozolomide (30 mg/Kg) | Sildenafil (100 mg/Kg) |
|---|---|---|---|---|---|
| 1 | 0.204 | | | | |
| 2 | 0.173 | | | 0.283 | |
| 3 | 0.244 | 0.541 | | 0.318 | 0.363 |
| 4 | 0.214 | | | | |
| 5 | 0.209 | | 0.414 | 0.311 | |
| 6 | 0.196 | | 0.405 | 0.286 | 0.309 |
| 7 | 0.214 | 0.336 | | 0.210 | |
| 8 | 0.211 | 0.434 | 0.350 | 0.237 | 0.220 |
| 9 | 0.232 | 0.511 | | 0.273 | |
| 10 | 0.188 | 0.368 | 0.407 | 0.343 | 0.259 |

TABLE 11-continued

Right Ventricle weight
Right Ventricle weight (gms)

| Animal no | Negative control | Positive control | Control | Temozolomide (30 mg/Kg) | Sildenafil (100 mg/Kg) |
|---|---|---|---|---|---|
| 11 | 0.218 | 0.382 | 0.404 | 0.232 | 0.256 |
| 12 | 0.170 | 0.341 | 0.335 | 0.245 | 0.308 |
| Mean | 0.206 | 0.416 | 0.386 | 0.274 | 0.286 |
| SD | 0.022 | 0.082 | 0.034 | 0.043 | 0.051 |
| SE | 0.006 | 0.031 | 0.014 | 0.013 | 0.021 |

Values are expressed as mean ± SE and analysed by one way ANOVA followed by Tukey's multiple comparison post-test.
* $P < 0.05$,  $P < 0.01$, * $P < 0.001$ as compared to control, + $P < 0.05$, ++ $P < 0.01$, +++ $P < 0.001$ as compared to positive control

TABLE 12

Right ventricle/Body weight
Right ventricle/Body weight

| Animal no | Negative control | Positive control | Control | Temozolomide (30 mg/Kg) | Sildenafil (100 mg/Kg) |
|---|---|---|---|---|---|
| 1 | 0.0005 | | | | |
| 2 | 0.0004 | | | 0.0011 | |
| 3 | 0.0006 | 0.0015 | | 0.0011 | 0.0012 |
| 4 | 0.0005 | | | | |
| 5 | 0.0005 | | 0.0012 | 0.0011 | |
| 6 | 0.0005 | | 0.0010 | 0.0010 | 0.0009 |
| 7 | 0.0005 | 0.0010 | | 0.0008 | |
| 8 | 0.0005 | 0.0012 | 0.0010 | 0.0007 | 0.0006 |
| 9 | 0.0006 | 0.0014 | | 0.0009 | |
| 10 | 0.0004 | 0.0011 | 0.0012 | 0.0008 | 0.0007 |
| 11 | 0.0005 | 0.0011 | 0.0012 | 0.0008 | 0.0007 |
| 12 | 0.0005 | 0.0011 | 0.0010 | 0.0009 | 0.0009 |
| Mean | 0.0005 | 0.0012 | 0.0011 | 0.0009 | 0.0008 |
| SD | 0.0000 | 0.0002 | 0.0001 | 0.0002 | 0.0002 |
| SE | 0.0000 | 0.0001 | 0.0000 | 0.0001 | 0.0001 |

Values are expressed as mean ± SE and analysed by one way ANOVA followed by Tukey's multiple comparison post-test.
* $P < 0.05$,  $P < 0.01$, * $P < 0.001$ as compared to control, + $P < 0.05$, ++ $P < 0.01$, +++ $P < 0.001$ as compared to positive control The results of the study suggest that Temozolomide activity in treatment of PAH was found to be comparable among with Sildenafil activity.

Example 3: Temozolomide Tablets

| Sr. No. | Ingredients | Qty/Tab (mg) |
|---|---|---|
| 1. | Temozolomide | 2.5-300 |
| 2. | Microcrystalline cellulose | 10-35 |
| 3. | Lactose anhydrous | 50-200 |
| 4. | Tartaric acid | 5-25 |
| 5. | Croscarmellose Sodium | 2-10 |
| 6. | Povidone | 3-10 |
| 7. | Polysorbate 80 | 3-10 |
| 8. | Isopropyl alcohol | q.s. |
| 9. | Colloidal Anhydrous silica | 1-5 |
| 10. | Talc | 1-5 |
| 11. | Magnesium Stearate | 1-5 |
| | Coating | |
| 12. | Opadry ready mix | 10-20 |
| 13. | Purified water | Qs |

Manufacturing Process

1. Temozolomide, Lactose anhydrous, microcrystalline cellulose, tartaric acid, croscarmellose sodium, were sifted through sieves and added to the rapid mixer granulator and mixed.
2. Polysorbate 80 was dissolved in small quantity of isopropyl alcohol and added to the dry mix blend of step 1 under constant mixing.
3. Binder solution was prepared by dissolving povidone in required quantity of Isopropyl alcohol under stirring to get clear solution.
4. The mixture of step 1 was then granulated using the binder solution of step 3 to form granules which were then dried in fluid bed processor and sizing of the granules was done by passing through sieves.
5. The sized granules were then blended with previously sifted silicon dioxide, talc in a suitable blender followed by lubrication with magnesium stearate.
6. The blend was then compressed into tablets using a tablet compression machine.
7. The tablets were then coated using a dispersion of opadry in purified water in a coating machine.
8. The coated tablets were then filled in suitable HDPE containers.

Example 4: Temozolomide Capsules

| Sr. No | Ingredients | Qty. (mg/unit) |
|---|---|---|
| 1. | Temozolomide | 2.5-300 |
| 2. | Lactose anhydrous | 75-400 |
| 3. | Tartaric acid | 5-25 |
| 4. | Colloidal silicon dioxide | 0.1-1.5 |
| 5. | Stearic acid | 0.1-15 |
| 6. | Empty hard gelatin capsule (No.) | 1 unit |

Manufacturing Process:

1. Temozolomide, lactose anhydrous, tartaric acid, were sifted through sieves and added to a blender and mixed.
2. Stearic acid and colloidal silicon dioxide were sifted through the suitable sieves and added to the blend of step 1 and blended.
3. The blend was then filled into hard gelatin capsule shells using a capsule filling machine and packed in a suitable container.

Example 5: Temozolomide Capsules

| Sr. No. | Ingredients | Quantity mg/tablet |
|---|---|---|
| 1. | Temozolomide | 2.5-300 |
| 2. | Pregelatinized corn starch | 10-50 |
| 3. | Colloidal silicon dioxide | 1-15 |
| 4. | Tartaric acid | 5-25 |
| 5. | Magnesium stearate | 3-15 |
| 6. | Talc | 3-15 |
| 7. | Empty hard gelatin capsule (No.) | 1 unit |

Manufacturing Process

1. Temozolomide was sifted using a sifter. Pregelatinized corn starch, tartaric acid, colloidal silicon dioxide and talc were also sifted separately. Both the sieved powders were mixed in a blender.
2. Magnesium stearate was sifted using a sifter and the above blend. The blend was further mixed.

3. The blend was then filled in the empty hard gelatin capsule shells using a capsule filling machine.

Example 6: Temozolomide Soft Gelatin Capsules

| Sr. No | Ingredients | Qty. (mg/unit) |
|---|---|---|
| 1. | Temozolomide | 2.5-300 |
| 2. | D-alpha-tocopheryl polyethylene glycol 1000 succinate (TPGS) | 50-400 |
| 3. | Polyethylene glycol 400 | 200-350 |

Manufacturing Process:
1. D-alpha-tocopheryl polyethylene glycol 1000 succinate (TPGS) was added in a suitable stainless steel-jacketed vessel and heated until liquefied.
2. Added polyethylene glycol and mix until homogenous solution was obtained.
3. Increased temperature and added temozolomide to the solution by stirring until temozolomide was dissolved.
4. Added remaining quantity of polyethylene glycol to the solution of step 3 and cooled to room temperature.
5. Vacuum was applied to remove air entrapped in the solution.
6. The solution was then filled in soft gelatin capsules using a capsule-filling machine.
7. The capsule shells were the dried until the desired moisture levels and packed in a suitable container.

Example 7: Temozolomide for Injection

| Sr. No | Ingredients | Qty. (mg/unit) |
|---|---|---|
| 1 | Temozolomide | 2.5-300 |
| 2 | Mannitol | 250-700 mg |
| 3 | L-threonine | 20160 mg |
| 4 | Polysorbate 80 | 120 mg |
| 5 | Sodium citrate dihydrate | 235 mg |
| 6 | Hydrochloric acid | 160 mg |
| 7 | Water for injection | |

Manufacturing Process:
1. Mannitol, L-threonine, polysorbate 80, sodium citrate dihydrate were added to the required quantity of water for injection and dissolved.
2. Hydrochloric acid was added to the solution of step 1 and mixed until a clear solution was obtained.
3. Temozolomide was added to the solution of step 1 and volume make up was done using water for injection
4. pH of the solution was measured and adjusted using Hydrochloric acid if required.
5. The solution was then filtered through filter and required quantity was filled in vials under aseptic condition and half stoppered using rubber closures.
6. The vials were then subjected to a lyophilization cycle to form a lyophilized product.
7. The vials were then completely stoppered with rubber closures under nitrogen atmosphere.
8. The stoppered vials were then sealed with aluminum caps.

Example 8: Temozolomide Powder for Oral Suspension

| Sr. No | Ingredients | Qty. mg/g |
|---|---|---|
| 1. | Temozolomide | 2.5-300 |
| 2. | Citric acid | 5-50 |
| 3. | Polysorbate 80 | 0.25-0.50 |
| 4. | Simethicone | 0.6-1.0 |
| 5. | Xanthan gum | 10-20 |
| 6. | Silicon dioxide | 7.5-12.5 |
| 7. | Titanium dioxide | 15-20 |
| 8. | Sodium benzoate | 6-10 |
| 9. | Cherry flavor, natural and artificial (microencapsulated) | 2.5-5.0 |
| 10. | Sucrose | q.s.t. 1000 mg |

Manufacturing process:
1. Temozolomide, citric acid, xanthan gum, silicon dioxide, titanium dioxide, sodium benzoate, cherry flavor and sucrose were sifted.
2. Required quantity of polysorbate 80 & simethicone were added on part of sifted sucrose and sifted.
3. The ingredients of step 1 & 2 were blended in an octagonal blender.
4. The blend was then filled in white translucent HDPE bottle with cap & sealed using induction sealer.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

The invention claimed is:
1. A method of treating pulmonary hypertension in a patient in need thereof, comprising administering to the patient a composition comprising an effective amount of temozolomide or a pharmaceutically acceptable salt or ester thereof, and at least one excipient.

2. The method of claim 1, wherein the pulmonary hypertension is pulmonary arterial hypertension.

3. The method of claim 1, wherein the patient has a resting pulmonary arterial pressure greater than 14 mm Hg.

4. The method of claim 1, wherein the patient has a resting pulmonary arterial pressure greater than 40 mm Hg.

5. The method of claim 1, wherein temozolomide is administered in an amount effective to lower resting pulmonary arterial blood pressure to a level no greater than 18 mm Hg.

6. The method of claim 1, wherein temozolomide is administered in an amount effective to lower resting pulmonary arterial blood pressure at least 5% relative to the resting pulmonary arterial blood pressure prior to commencing treatment.

7. The method of claim 1, wherein temozolomide is administered in a dose from 0.1 to 50 mg.

8. The method of claim 1, wherein the composition comprises temozolomide hydrochloride.

9. The method of claim 8, wherein the composition is administered orally, by injection, parenterally, buccally, transdermally, or by inhalation.

10. The method of claim 8, wherein the composition is administered orally.

11. The method of claim 8, wherein the composition is administered parenterally.

12. The method of claim 1, further comprising administering at least one additional agent effective to treat pulmonary hypertension.

13. The method of claim 12, wherein the at least one additional agent comprises one or more of phosphodiesterase inhibitors, calcium channel blockers, endothelin receptor antagonists, inotropic agents, prostacyclin pathway agonists, anti-coagulants, guanylate cyclase stimulators, PDE-5 inhibitors, or a combination thereof.

14. The method of claim 12, wherein the at least one additional agent comprises one or more of avanafil, lodenafil, mirodenafil, sildenafil, tadalafil, vardenafil, udenafil, zaprinast, icariin, amlodipine, nifefipine, diltiazem, bosentan, ambrisentan, sitaxsentan, macitentan, riociguat, toprimate, fusadil, warfarin, digoxin, epoprostenol, treprostinil sodium, iloprost, selexipag, or a combination thereof.

15. A pharmaceutical composition comprising temozolomide or a pharmaceutically acceptable salt or ester thereof, and at least one additional agent effective to treat pulmonary hypertension.

16. The pharmaceutical composition of claim 15, wherein the at least one additional agent comprises one or more of phosphodiesterase inhibitors, calcium channel blockers, endothelin receptor antagonists, inotropic agents, prostacyclin pathway agonists, anti-coagulants, guanylate cyclase stimulators, PDE-5 inhibitors, or a combination thereof.

17. The pharmaceutical composition of claim 15, wherein the at least one additional agent comprises one or more of avanafil, lodenafil, mirodenafil, sildenafil, tadalafil, vardenafil, udenafil, zaprinast, icariin, amlodipine, nifefipine, diltiazem, bosentan, ambrisentan, sitaxsentan, macitentan, riociguat, toprimate, fusadil, warfarin, digoxin, epoprostenol, treprostinil sodium, iloprost, selexipag, or a combination thereof.

18. A kit comprising temozolomide or a pharmaceutically acceptable salt or ester thereof, in an amount effective to treat pulmonary hypertension, and at least one additional agent effective to treat pulmonary hypertension.

19. The kit of claim 18, wherein the at least one additional agent comprises one or more of phosphodiesterase inhibitors, calcium channel blockers, endothelin receptor antagonists, inotropic agents, prostacyclin pathway agonists, anti-coagulants, guanylate cyclase stimulators, PDE-5 inhibitors, or a combination thereof.

20. The kit of claim 18, wherein the at least one additional agent comprises one or more of avanafil, lodenafil, mirodenafil, sildenafil, tadalafil, vardenafil, udenafil, zaprinast, icariin, amlodipine, nifefipine, diltiazem, bosentan, ambrisentan, sitaxsentan, macitentan, riociguat, toprimate, fusadil, warfarin, digoxin, epoprostenol, treprostinil sodium, iloprost, selexipag, or a combination thereof.

21. The kit according to claim 18, comprising a first composition comprising temozolomide or pharmaceutically acceptable salt or ester thereof, and a second composition comprising the at least one additional agent effective to treat pulmonary hypertension.

* * * * *